(12) United States Patent
Kurth

(10) Patent No.: US 6,887,229 B1
(45) Date of Patent: May 3, 2005

(54) METHOD AND APPARATUS FOR INSERTION OF ELONGATE INSTRUMENTS WITHIN A BODY CAVITY

(75) Inventor: Paul Kurth, Ranho Palos Verdes, CA (US)

(73) Assignee: Pressure Products Medical Supplies Inc., Santa Barbara, CA (US)

( * ) Notice: Subject to any disclaimer, the term of this patent is extended or adjusted under 35 U.S.C. 154(b) by 501 days.

(21) Appl. No.: 09/708,150

(22) Filed: Nov. 7, 2000

(51) Int. Cl.$^7$ .............................................. A61M 25/00
(52) U.S. Cl. ........................ 604/525; 604/530; 604/531
(58) Field of Search .......................... 604/164.01, 264, 604/510, 523, 95.05, 525, 164.13, 526, 167.01–167.05, 604/527, 528, 530, 531, 532; 606/108; 264/512–516, 264/563–569

(56) References Cited

U.S. PATENT DOCUMENTS

| | | | |
|---|---|---|---|
| 5,122,154 A * | 6/1992 | Rhodes | 623/1.13 |
| 5,395,341 A * | 3/1995 | Slater | 604/164.03 |
| 5,882,346 A * | 3/1999 | Pomeranz et al. | 604/525 |
| 6,090,072 A * | 7/2000 | Kratoska et al. | 604/164.01 |

* cited by examiner

*Primary Examiner*—Nicholas D. Lucchesi
*Assistant Examiner*—Catherine S. Williams
(74) *Attorney, Agent, or Firm*—Daniel L. Dawes; Myers Dawes Andras & Sherman

(57) ABSTRACT

A sheath is composed of a biocompatible material which has a stiffness and moldability such that it can easily be deformed by hand by the physician prior to implantation, or by means of a guiding or shaping tool such as the dilator, stylet and or guide wire during placement within the body cavity. Similarly, it has a suppleness such that it may be molded by its disposition within the body cavity without trauma to the tissues. Yet, it has sufficient stiffness and moldability such that it retains a shape which has been imparted to it by a shaping tool when in the body cavity, even when left unsupported or unconfined in a body cavity or subject to normal bodily fluid, blood or air flow. However, once the shaping or forming tool has been removed, the sheath will tend to stay in its molded shape in a body cavity without generating a resilient force or displacement which returns it to its original shape. A medical instrument can then be telescopically disposed through the sheath and thus correctly delivered within the body cavity according to the molded shape imparted to the sheath by the shaping tool. Further, the removal of the sheath similarly will not dislodge the medical instrument from its implanted position by the application of resilient forces or displacement arising during the removal of the sheath.

30 Claims, 3 Drawing Sheets

METHOD AND APPARATUS FOR INSERTION OF ELONGATE INSTRUMENTS WITHIN A BODY CAVITY

BACKGROUND OF THE INVENTION

1. Field of the Invention

The present invention is directed to the field relating to apparatus and methods used to insert of medical devices in a human or animal body, and in particular apparatus and methods used to insert medical devices into a vascular system or other anatomical cavities.

2. Description of the Prior Art

Development of permanent implantable catheter systems and temporary diagnostic and therapeutic catheters has resulted in life-saving benefits and has greatly improved the quality of life of patients virtually across the entire spectrum of medical treatment. The use of such permanent and temporary catheters in cardiology is a prime, but no means limiting example. In most cases, the catheter must be implanted at the site of application through the use of an introducer. Very often the introducer must be implanted or steered through a tortuous path and positioned at a site some distance from the proximal insertion point. Once the introducer is correctly positioned, an elongate medical instrument is then lead or fed through the introducer, perhaps with the further assistance of guidewires to place it or a selected portion of it at the target site. With the medical instrument correctly positioned, the introducer is then removed leaving the medical instrument in position.

However, the positioning of the medical instrument can be very delicate. Any force or displacement imparted to the medical instrument by withdrawal of the introducer can potentially dislodge the medical instrument from its intended position, which in turn can be reachieved only with additional procedures of varying difficulty, if at all.

U.S. Pat. No. 4,467,817 to Harris discloses a small diameter pacing lead of carbon filaments surrounded by a stiffening sheath. The tip of the pacing lead extends beyond the stiffening sheath whereby the stiffening sheath is positioned behind the tip of the pacing lead to assist guiding the pacing lead into the desired organ.

U.S. Pat. No. 5,639,276 to Weinstock et. al. describes a cardiac introducer which as a gradient of stiffness along its length so that it is sufficiently soft or flowable at its distal end so that it can pass through the tricuspid valve without causing trauma and is proximally sufficiently stiff so that it can be forced through a tortuous venous path into the apex of the right ventricle of the heart. Nothing is taught in Weinstock or Harris regarding the moldability of the introducer which would allow a reliable lead placement or reliable introducer withdrawal.

A single preshaped guide is frequently inadequate to reach a desired location due to large anatomical variations within the body. What is needed is an apparatus and method for the stable placement of a medical instrument in a body cavity with which apparatus and method there is a decreased risk of inappropriate lead placement, dislodgment of either the implanted medical instrument by withdrawal of the introducer, dislodgment of the introducer by withdrawal of a shaping tool or other placement device, and the ability to be shaped to conform to the individual's anatomy to reach the desired location.

BRIEF SUMMARY OF THE INVENTION

The illustrated embodiment of the invention shows a guiding sheath made of a moldable material which is not resilient, or at least has a limited resiliency returning it to its original shape once deformed from that original shape. In other words, the sheath does not necessarily retain its original shape, but tends to assume and keep the new shape which has been later imparted to it. This is referred to as moldability. The material from which the sheath is made and/or its construction renders the sheath more moldable in that it is able to retain a new shape when or after being placed in the body, typically without the on-going aid of shape retaining devices such as obturators, guidewires, steering devices, stylets and the like.

The sheath may be molded by the clinician before being placed in the body, or it may change its resiliency or moldability just before or after being placed in the body when it is exposed to water, temperature, light or any combination of such exposures. The material comprising the sheath becomes moldable and retains its new shape either by being placed within the body, or otherwise changes its moldability by means of a treatment of the material of the sheath just prior to being implanted or from being implanted in the body.

The guiding sheath may have any number of different physical forms, such as a moldable elongate tube with braided reinforcement at selected sections of its length, reinforcing fibers disposed on the sheath for improved kink resistance and to aid in the maintenance of a new shape, or it may have a moldable sheath body which is splittable, peelable, tearable by tearing along least one score line or by virtue of the nature of the material itself. It is also contemplated that the guiding sheath may not be peelable or separable, but may need to be cut with a cutting tool. It may be preshaped or straight when first introduced. It may be made of the same material along its entire length or made of moldable material of various stiffness at various sections along its length. The stiffness of a moldable section can be altered by varying its thickness, disposing tubes within tubes, layering it or bonding different layers of different stiffness together. These examples by no means exhaust the different ways in which the stiffness of the sheath or any selective portion of it may be manipulated. Any means now known or later devised for such a purpose is expressly contemplated as being within the scope of the invention and equivalent to the disclosed means.

The guiding sheath may contain at least one segment of variable length made of a material which is not moldable. The material which is used that is not moldable may similarly be of various stiffness by altering its thickness, diameter or its chemical makeup and may have varying resiliency. Again such a nonmoldable section may be made of materials of various stiffness and resiliency which are bonded together or have their stiffness and resiliency altered by layering of materials each with a different stiffness or resiliency, by positioning tubes of variable diameters inside of each other, or by use of variable thickness materials to alter the stiffness and resiliency of the section.

The sheath may contain wires for deflection and positioning, but which are not used to retain the shape of the catheter. It may have a soft tip, it may have an ultrasound imaging distal tip and/or it may contain at least one electrical conductor. The guiding sheath may contain at least one electrode for sensing or delivering energy, or may contain at least one fiber optic wire. The sheath may also be provided with at least one distal balloon. The balloon disposed on the sheath may be separable from sheath along score lines or may be cut off or otherwise removable from sheath.

The guiding sheath may contain at least one lumen and at least one vent. The guiding sheath may contain a proximal sealing valve with or without a side port, and a sealing valve which may be separable, tearable or not separable. The sealing valve may be attachable or detachable to the sheath.

Use of the guiding sheath may require a steering or shaping tool for molding or guiding of sheath. The shaping tool may contain a handle and at least one wire for deflection or steering of the tip of the tool. The shaping tool may be preshaped and may or may not contain a mechanical steering mechanism. The shaping tool may also have a soft tip and may contain at least one lumen with at least one vent. The lumen of shaping tool may be used for infusion of a liquid and or for passage of a guide wire. As is the case with the sheath, the shaping tool may contain at least one balloon, and at least one electrode for sensing or delivering energy.

The sheath may be nonmoldable, but flexible so that it can be steered or guided using a steering or guiding tool to a physician selected site, and then after implantation of a medical instrument through the sheath, peeled away from the medical instrument.

It is to be expressly understood that the claims are defined so as not to be construed as limited in any way by the construction of "means" or "steps" limitations under 35 USC 112, but to be accorded the full scope of the meaning and equivalents of the definition provided by the claims. The invention can be better visualized by turning now to the following drawings wherein like elements are referenced by like numerals.

Figure 1A:
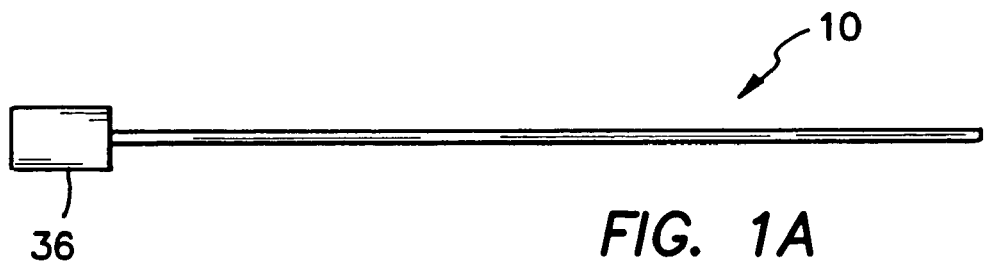
FIGS. 1a–1d are side elevational views of the sheath in which the sheath is composed of a moldable material showing how a series of bends of differing nature can be molded into the compound shape of the sheath.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

A prebiased introducer or sheath can be steered or manipulated by a number of means to a designated site within a body cavity, such as the coronary sinus in the heart. However, due to large anatomical variation in individual patients and difficulty of maneuver in the venous system, the small size of the coronary sinus and its anatomy, exact placement of an introducer in the coronary sinus even with a prebiased introducer is frequently not possible and if placed, its retention therein for delivery of a medical instrument is often not reliable. For example, patients with cardiomyopathy typically have a heart one-and-a-half to two times the normal size. In such cases conventional fixed, preshaped introducers must often be forcibly deformed by considerable amounts in order to be properly placed. When such introducers are placed in the coronary sinus the risk of dissection of the vein becomes unacceptable due to the shearing forces applied by the torque of a preshaped catheter. Dissection of the coronary sinus can have serious or fatal consequences. What is needed is an introducer which can be custom-shaped as it is being implanted into each patient so as to accommodate each individual's anatomy and then once appropriate placement is achieved, then remain in position with the custom shape imparted to it without torque or shearing forces being present until the medical instrument, or in this example, the pacemaker lead, is safely delivered to the coronary sinus.

Although the illustrated embodiment is sometimes characterized as a cardiac application using the sheath of the invention or in particular an implantation into the coronary sinus, it is expressly understood that the medical applications to which the sheath may be put is entirely general and not limited to even cardiac applications. For example, the guiding sheath may be used to deploy permanent pacemaker leads into various areas of the heart such as the right atrial appendage, the intra atrial septum, the lateral atrial wall, the right ventricle, the intra ventricular septum, as well as the right ventricular outflow tract. Other areas of the heart can be accessed such as the left atrium either through an intra atrial puncture or retrograde through the left ventricle. Equipped with an ultrasound probe the walls of the heart can be imaged and more precise placement of an ablating probe can be accomplished. Having a moldable coronary angioplasty guide for delivery of coronary and venous graft devices would also be of benefit.

Other body areas in which a moldable catheter would be of significant value are the brain, where deployment of stents, coils or other diagnostic and therapeutic devices would be of value. A moldable guide for delivery of renal stents, arterial devices such as aortic stents and peripheral arterial devices and stents would be of value. Moldable catheters for use as nephrostomy drainage catheters, gall bladder drainage catheters, liver drainage catheters would be useful.

FIG. 1a is a diagrammatic perspective view showing an introducer or sheath 10 of the invention which has been initially provided in a straight form. In the illustrated embodiment sheath 10 is shown as a hollow cylinder in which a central main lumen is defined. However, it is to be expressly understood that what will be referred to as "sheath 10" should be understood to also include an elongate member which may be solid or have only minor lumens defined therein, like a catheter. In the case where sheath 10 does not include a central lumen, the shaping tool used with sheath 10 will then be an elongate tube which is telescopically disposed over sheath 10 instead of being an elongate cylinder disposed in the central lumen of sheath 10.

In the simplest illustrated embodiment sheath 10 is composed of a single kind of biocompatible material which is moldable. When speaking about resiliency what is meant is the tendency of material to return to its original shape like a spring. The stiffness of a material is independent of its resiliency and refers to the force required to deform an object. Thus, an object may be stiff, while not being resilient like common iron, or may not be stiff and also not resilient like malleable lead wire. A weak coil spring would thus not be stiff, but would be resilient, while a strong coil spring would be both stiff and resilient. The stiffness of the material is the resistance the material to a change in its shape, which stiffness is independent of its resiliency. Materials may be very stiff, but when once deformed do not return to their original undeformed shape. It is also possible to have a material which has a low stiffness, i.e. can be easily deformed, and have a high or low resiliency tending to return them to their original shape or not respectively.

The stiffness and moldability of the material of the preferred embodiment is such that it can easily be deformed by hand by the physician prior to implantation, by means of a guiding or shaping tool such as a steerable or shaped dilator, stylet and/or guide wire during placement within the body, or by molding wires embedded in the sheath. For example, in the preferred embodiment sheath 10 is initially implanted into the vascular system with the aid of a dilator as is conventional in the art, which dilator is used to open the vascular puncture to allow sheath 10 to be telescopically disposed over the dilator and smoothly accepted into the punctured vessel while maintaining good blockage against blood loss. While the dilator is conventionally disposed through a central longitudinal lumen defined through the length of the sheath, it is also within the scope of the invention that the reverse may be true, namely that the sheath is disposable through a central longitudinal lumen defined through the length of the dilator. "Shape memory" is defined within this specification as the tendency of a material to retain a new shape once molded to the new shape or configuration. Shape memory is thus a characteristic which is distinguished from stiffness. An object can lack resiliency without having high shape memory. For example, a soft, completely limp catheter tip, has no substantial resiliency and may not have any substantial shape memory either. By the same token a different type of soft catheter tip may be fabricated according to the invention to have high shape memory and hence would also not have any substantial resiliency.

Similarly, a sheath fabricated according to the invention would have a suppleness such that it may be molded by its disposition within the body cavity without trauma to the tissues. Yet, it has sufficient shape memory such that it retains a shape which has been imparted to it by a shaping tool when in the body, even when left unsupported or unconfined in a body cavity or subject to normal bodily fluid, blood or air flow. A material would have "moldability" or be "moldable" in the context of this specification, if its shape could be changed without difficulty before or during a medical procedure, and if it had sufficient shape memory to hold its new shape in such circumstances.

For example, if applied to the heart, material of the sheath will be such that it will tend to mold itself to the shape of the confined vascular pathway into which it has been disposed. However, once the guiding or forming tool has been removed, sheath 10 will tend to stay in its molded shape in a heart chamber without generating a resilient force or displacement which returns it to its original shape. A catheter or other elongate medical instrument (not shown) can then be telescopically disposed through sheath 10 and thus correctly delivered within the body according to the molded shape imparted to sheath 10 by a shaping tool 42. Further, the removal of sheath 10 similarly will not dislodge the medical instrument from its implanted position by the application of resilient forces or displacement arising from the movement of sheath 10 relative the medical instrument during the removal of the sheath.

Figure 1B:
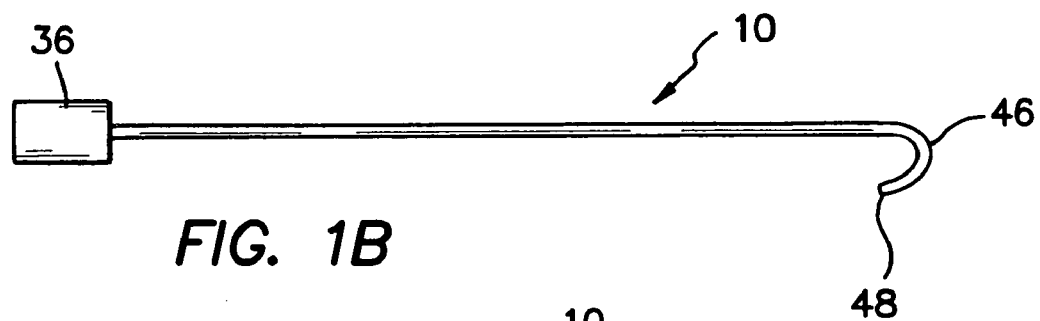

FIG. 1*a* depicts sheath 10 as originally manufactured so as to be straight and to be provided with a proximal nonsealing hub or sealing hemostatic valve 36. FIG. 1*b* is a side elevational view of sheath 10 of FIG. 1*a* in which an acute bend 46 has been molded into sheath 10 near distal tip 48. Bend 46 can be formed outside the body or within the body by any of the means disclosed in this specification and means equivalent thereto. In the preferred embodiment, an approximate shape is formed by hand by the attending physician when sheath 10 is outside the body and then it is fine tuned to the final shape using a shaping tool after being implanted in the body or heart.

Figure 1C:
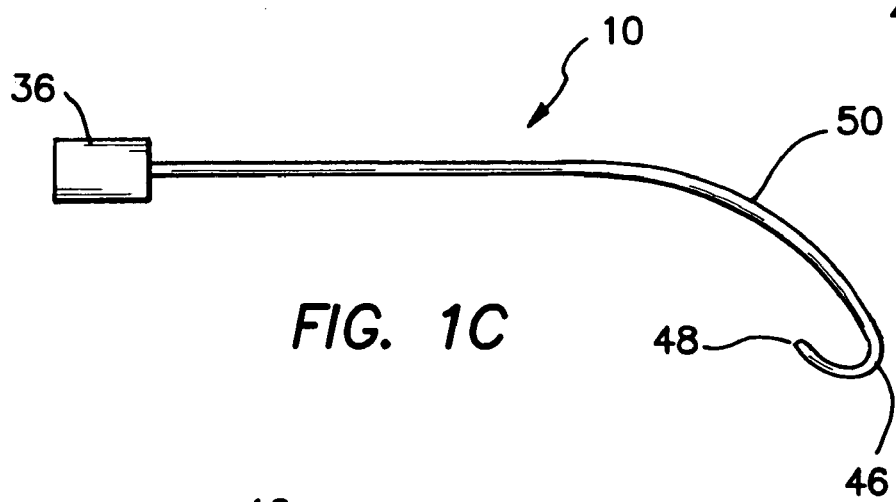

FIG. 1*c* is a side elevational view of sheath 10 of FIG. 1*b* in which a slightly less acute bend 50 has been molded into sheath 10 at a more proximal position than bend 46. Again, in the preferred embodiment, an approximate shape is formed by hand by the attending physician when sheath 10 is outside the body and then it is fine tuned to the final shape or bend 50 using a shaping tool after being implanted in the body, or body cavity such as the heart.

Figure 1D:
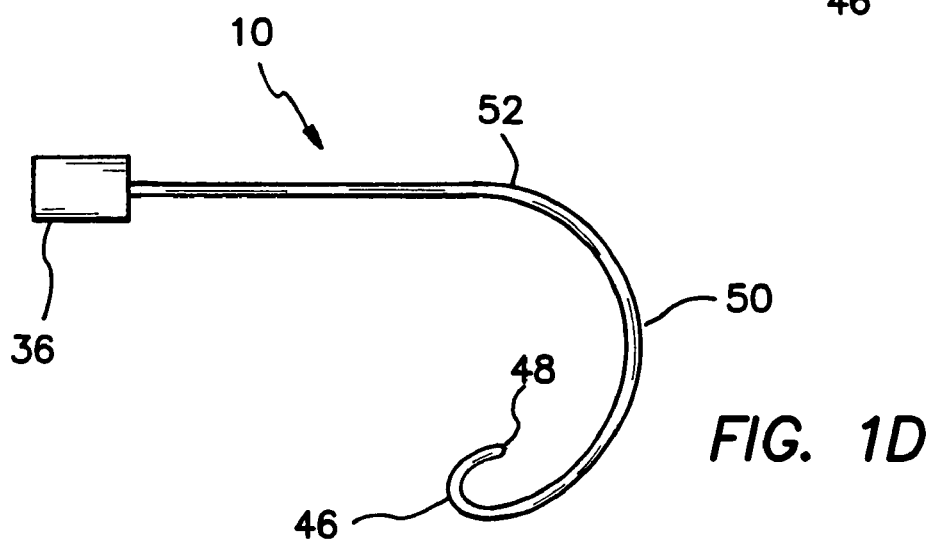

Finally, FIG. 1*d* is a side elevational view of sheath 10 of FIG. 1*c* in which an even less acute bend 52 has been molded into sheath 10 at a more proximal position than bend 50. Thus, it can be readily appreciated that compound and complex bends or shapes can be imparted to sheath 10 according to the invention in a manner which is individualized to each application and to each patient.

Many materials may suffice for this use provided they have the requisite degree of stiffness, moldability or lack of the memory shape. For example one class of materials which may be satisfactory are those materials termed a thermoplastic urethane (TPU) sold by Thermedics Polymer Products of Woburn, Mass. Such TPU materials include, but are not limited to, families of aliphatic polyether based thermoplastic urethane resins, which can be formulated to absorb water, aromatic polyether based thermoplastic urethanes, and aliphatic polycarbonate based thermoplastic urethanes, all of which are available with a wide range of durometers, colors and radiopacifiers. These resins are easy to process and do not yellow upon aging. Solution grade versions are candidates for replacement of latex.

The common characteristic of these materials is that their moldability increases with temperatures normally found within the body range or with exposure to water moisture or light. Thus, the proximal portion of sheath 10, when made from these temperature, moisture or light sensitive materials, may remain stiffer and more resilient than the distal portions which have been implanted into the body and exposed to a higher temperature and/or moisture. The change in stiffness and resilience, or the change in moldability is not instantaneous, but occurs over a period of time during the medical procedure. Therefore, sheath 10 remains nonmoldable and stiff enough to be steerable or guideable during the placement procedure. After being implanted it becomes moldable and with the use of a guiding tool it can be guided to its target location. The medical device can then be disposed through sheath 10. Even in cases where the change in moldability is fast, any conventional shaping and/or guiding tool, well known to the art, can be used to support sheath 10 during its implantation and used to impart a specific shape to it in preparation for its use to deliver a medical instrument.

However, when sheath 10 is to be removed, it has had sufficient time to respond to the elevated temperature, moisture or previous exposure to light to increase its moldability. Sheath 10 may then be slid off the medical instrument without then imparting a disturbing force to the medical instrument that would cause it to be dislodged from the target site.

Figure 2:
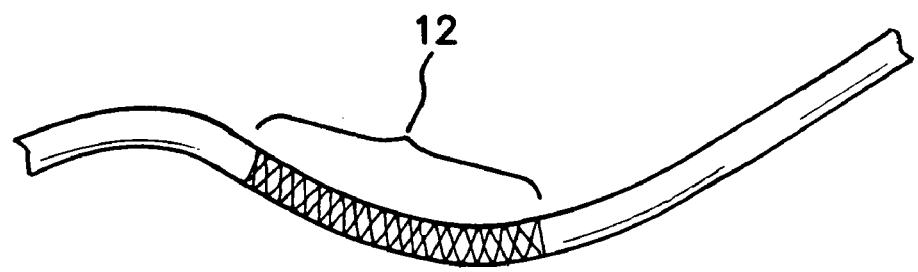
FIG. 2 is a side elevational view of the sheath in which a portion has been reinforced by a woven or braided reinforcement or braiding to help retain the new shape and to make the sheath axially more rigid.
Figure 3:
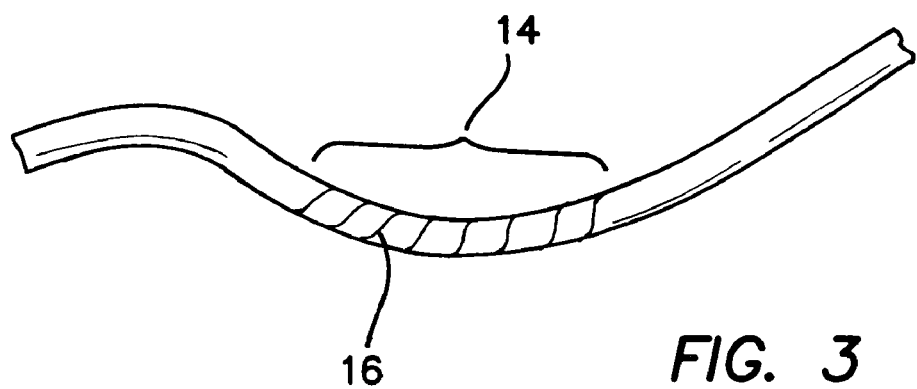
FIG. 3 is a side elevational view of the sheath in which a portion has been reinforced by fiber to add axial strength and to help retain molded shape.

Thus it is expressly understood that sheath 10 of FIG. 1, in addition to being composed of homogeneous material or of temperature, light or moisture sensitive material, may be comprised of a plurality of different materials or composition of the same or different materials in different physical forms. For example, one or more sections 12 of sheath 10 may include reinforced or braided fibers which will give sheath 10 a selective stiffness or resilience along its length as shown in diagrammatic view in FIG. 2. In another embodiment as shown in FIG. 3 reinforcing fibers 16 may be provided on a section 14 of sheath 10 to provide kink resistance. Both means of reinforcement also assist in retaining new shapes. Different sections of sheath 10 may also be provided with different moldability by being made out of different materials which are bonded or layered together, by telescopically positioning tubes of different diameters inside each other, or by using sections or layers of variable thickness. Thus, sheath 10 may be itself manufactured with a varying integral wall thickness.

Figure 4:
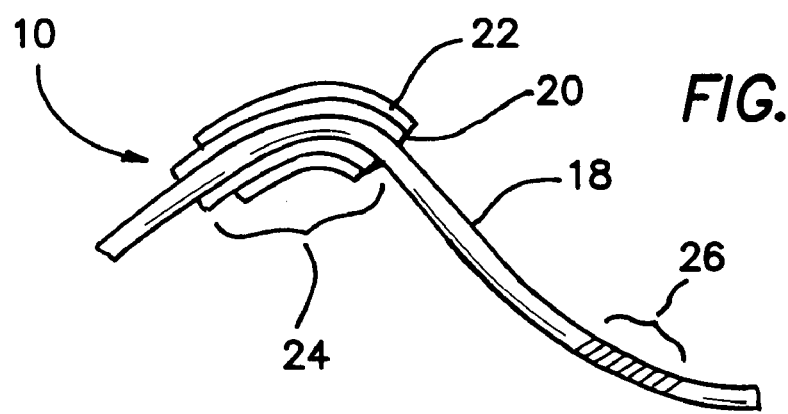
FIG. 4 is a side elevational view of the sheath in which a portion of the sheath is stiffened by layering concentric material around the exterior of the sheath.

FIG. 4 is a side cross sectional view in enlarged scale and which shows a section 24 of sheath 10 which is comprised of three telescopically disposed layers 18, 20 and 22 to provide a thickened and therefore stiffer section 24 then could be realized than using a single layer 18. Thus it is to be understood that sheath 10 may be provided with a moldable or nonmoldable section of arbitrary length which may have variable stiffness. In this manner, sheath 10 may be comprised of preshaped nonmoldable sections and moldable sections according to the application in question. Sheath 10 may be supplied in an originally straight shape or may be preshaped during original manufacture.

The shape memory or moldability of sheath 10 may also be altered not only by building up a composite thickness such as shown in section 24 of FIG. 4, but also by chemically altering the composition of a section, such a section 26 of sheath 10. Thus, sheath 10 may have a section 26 which is chemically treated or exposed to radiation to change its moldability or to prevent it from becoming moldable. The change may be such as to either increase or decrease these characteristics.

Sheath 10 may be splittable, peelable, or tearable. It may be comprised material which naturally tears along the preferred line, namely the longitudinal direction of sheath 10, or sheath 10 may be scored so that it preferentially tears along score line as is well-known in the art. In this manner sheath 10 may be peeled away or otherwise removed from the medical instrument after its implantation without the need for sliding sheath 10 over the proximal end of the medical instrument. The possibility that sheath 10 may be peeled away does not exclude, of course, the option that sheath 10 may be cut away by a scalpel or a sheath splitter well-known to the art. In such a latter case, sheath 10 may be integral and not peelable or separable from the medical instrument other than by sliding it over the proximal end of the instrument or by cutting it away.

Figure 5:
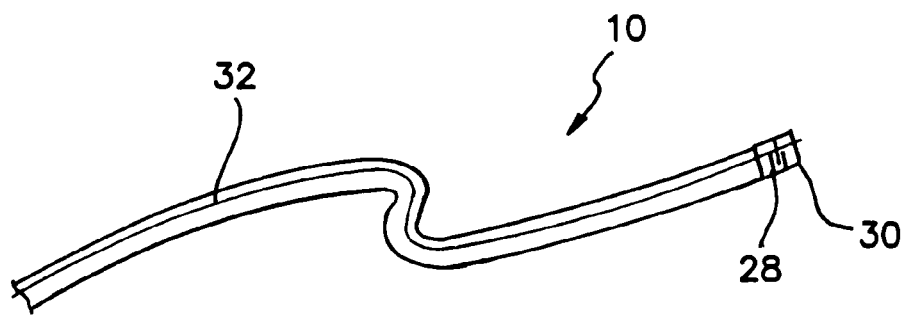
FIG. 5 is a side elevational view of the sheath in which at least one conductor or wire is disposed along its length and coupled to a diagnostic or therapeutic device such as an ultrasound imager.

It is also to be expressly understood that sheath 10 may include many additional structures used for deflection, steering and guiding. For example, sheath 10 may contain wires for deflection and positioning which are not used to retain the shape of the catheter which is inserted into it, such as shown by Savage et. al., "Steerable Catheter," U.S. Pat. No. 5,507,725 (1996), incorporated herein by reference. The wire or wires included within sheath 10 may be used to provide a conducting part a circuit, alone or in combination with being used for deflection and positioning. The tip of sheath 10 may also include a plurality of active diagnostic or therapeutic devices such as an ultrasound imaging tip as diagrammatically depicted in FIG. 5. Ultrasound imaging device 28 is mounted on or near distal tip of 30 of sheath 10 and is connected to the proximal end of sheath 10 by means of a conductor or wire 32 imbedded within the wall of sheath 10. In addition to one or more wires dispose within sheath 10, sheath 10 may be provided with one or more optical fibers for use with a photonic device mounted at or near the distal tip of sheath 10.

Figure 6:
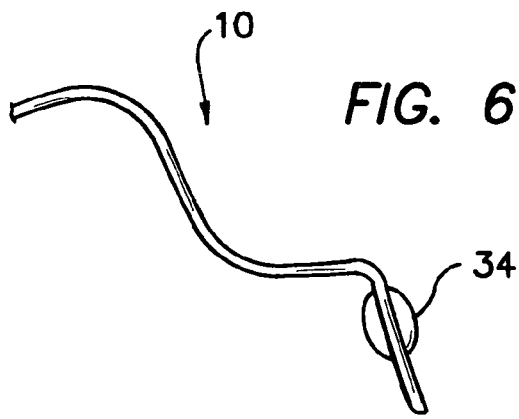
FIG. 6 is a side elevational view of the sheath in which a lumen is defined longitudinally through the sheath and communicated to a balloon disposed on the sheath.
Figure 7:
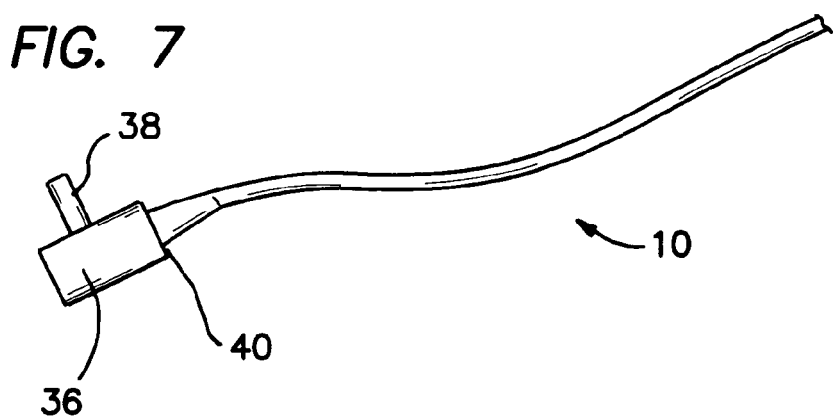
FIG. 7 is a side elevational view of the sheath in which a proximal sealing valve and side arm port is provided.

Sheath 10 may be provided not only with distal electrical devices but also with actuatable mechanical structures or devices, such as an inflatable distal balloon 34 as diagrammatically shown in FIG. 6. Balloon 34 may be mounted at any point on sheath 10, beginning at the distal tip rearwards. Balloon 34 is then communicated with a lumen defined within sheath 10 to provide for its inflation and deflation. Balloon 34 may be separable from sheath 10 by also being splittable along score lines defined in sheath 10 along its longitudinal axis, or may be cut off by use of a scalpel or other cutting tool. Balloon 34 may be removed from sheath 10 by any means now known or later devised.

The same lumen used to inflate or deflate balloon 34 may also be used as a lumen for delivery or removal of fluids through sheath 10. One or more vents may then be provided or defined through sheath 10 as exit and/or entry orifices for such a lumen.

The proximal end 40 of sheath 10 of may also be provided with a sealing valve 36 with or without the provision of a side port 38 through which fluids may be provided to and from the lumens defined within sheath 10. Sealing valve 36 may or may not be separable, splittable, or tearable from sheath 10.

Figure 8:
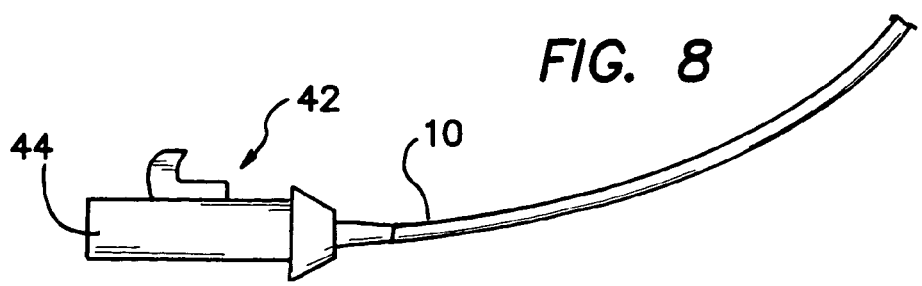
FIG. 8 is a side elevational view of a steerable shaping tool which is telescopically disposed in the sheath.

In some applications sheath 10 may we require a shaping tool to assist in its implantation within the body. The shaping tool, generally denoted by reference numeral 42, may contain a handle 44 and at least one or more wires to deflect at least the distal tip portion of the shaping tool, such as shown in diagrammatic view in FIG. 8. While tool 42 is shown in FIG. 8 as not having a prebiased shape and as being mechanically steerable, it is also within the scope of the invention that such shaping tool 42 may be manufactured with a predetermined shape or biased and may not have a mechanical steering mechanism. As with sheath 10, shaping tool 42 may be provided with a soft or completely pliable or moldable tip and may incorporate one or more lumens with corresponding vents within the elongate tool body. Just as for sheath 10, any lumens provided in shaping tool 42 may be used for infusion of a liquid or for passage of a guide wire there through. So too may shaping tool 42 contain at least one inflatable balloon at or near its distal tip and at least one electrode for sensing signals along the length of shaping tool 42 or for delivery of energy through a distal electrode.

Although the preferred embodiments have been at least in part moldable, it is also within the scope of the invention that a peel-away, flexible and nonmoldable sheath may be used in combination with a steering and/or guiding tool. Such a peel-away sheath 10 would be flexible enough so that it could be practically guided to a target site selected by the physician by an obturator, guidewire, steering device, stylet 42 or the like, namely selectively shaped or guided to a selected site like the coronary sinus. Sheath 10 need not be moldable and would normally be provided in an initially straight shape or form. Its shape would then be determined or changed according to the application to which it is applied by means of steering and guiding tool 42. Sheath 10 could then be separated from tool 42 by being peeled off along a longitudinal score line, or by tearing along a preferred direction of tear characteristic of the material of which sheath 10 is composed. As with other embodiments, sheath 10 may be used with or without a proximal sealing valve, distal balloons, and distal therapeutic or diagnostic devices. In the case where a distal balloon is used, it is splittable with sheath 10.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An apparatus comprising:
   a moldable sheath configured to at least temporarily retain a specific shape selectively imparted to it by a user by bending of the sheath along its length; and
   a shaping tool arranged and configured to be applied to said moldable sheath to impart said specific shape to said sheath while within a body cavity, which specific shape is held without continued inserted presence of said shaping tool in the sheath.

2. The apparatus of claim 1 where said shaping tool is separate from said sheath.

3. The apparatus of claim 1 where said shaping tool is incorporated within said sheath.

4. The apparatus of claim 1 further comprising a sealing valve coupled to said sheath to seal said lumen.

5. The apparatus of claim 1 where said sheath has at least one portion with a stiffness different than remaining portions of said sheath.

6. The apparatus of claim 1 where said sheath has at least one portion with a moldability different than remaining portions of said sheath.

7. The apparatus of claim 1 where said sheath is deployed in a body cavity and has at least one portion with a moldability which can be altered at the time of implantation in said body cavity.

8. The apparatus of claim 7 where said at least one portion has its moldability altered before said sheath is implanted into said body cavity.

9. The apparatus of claim 7 where said at least one portion has its moldability altered after said sheath is implanted into said body cavity.

10. The apparatus of claim 1 where said sheath is characterized by a sufficient moldability so that removal of said shaping tool does not result in any 3substantial displacement of said sheath from said specific shape.

11. The apparatus of claim 1 where said sheath has a lumen and where said shaping tool applied to said sheath comprises an elongate shaping tool which is telescopically disposed within said lumen in said sheath.

12. The apparatus of claim 1 where said moldable sheath has at least a portion of changed moldability relative to remaining portions of said sheath.

13. The apparatus of claim 12 where said portion which changes its moldability while in said body cavity comprises at least a portion of said sheath having a moldability dependent on temperature in which said moldability of said sheath is changed while in said body cavity and exposed to a body cavity temperature elevated above ambient temperature.

14. The apparatus of claim 12 where said portion of changed moldability has its moldability changed by treating at least a portion of said sheath exterior to said body cavity prior to implanting.

15. The apparatus of claim 1 where said moldable sheath is preshaped according to its intended application within said body cavity.

16. The apparatus of claim 1 where said sheath has a proximal end and further comprising a sealing valve disposed on said proximal end.

17. The apparatus of claim 16 where said sealing valve is integral with said sheath.

18. The apparatus of claim 16 where said sealing valve is separate from said sheath.

19. The apparatus of claim 1 further comprising at least one wire disposed in said sheath and usable for deflecting and positioning said sheath.

20. The apparatus of claim 1 where said shaping tool is steerable.

21. The apparatus of claim 1 where said shaping tool comprises a guidewire.

22. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool, where said shaping tool applied to said sheath comprises a shaping tool applied exteriorly to said sheath and imposing a shaping force thereon.

23. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool,
where said moldable sheath has at least a portion of changed moldability relative to remaining portions of said sheath,
where said portion which changes its moldability while in said body cavity comprises at least a portion of said sheath having a moldability dependant on temperature in which said moldability of said sheath is changed while in said body cavity and exposed to a body cavity temperature elevated above ambient temperature, and
where said portion which changes its memory shape while in said body cavity comprises at least a portion having a moldability dependent on moisture in which said moldability of said sheath is changed while in said body cavity and exposed to moisture.

24. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool,
where said moldable sheath has at least a portion of changed moldability relative to remaining portions of said sheath,
where said portion of changed moldability has its moldability changed by treating at least a portion of said sheath exterior to said body cavity prior to implanting, and
where said portion of changed moldability has its moldability changed by exposing at least a portion of said sheath to radiation.

25. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool, where said moldable sheath has a tip portion and where said tip portion is substantially soft and compliant without appreciable moldability.

26. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool, where said shaping tool has a tip portion which is substantially soft and compliant without substantial moldability rendering it nontraumatic.

27. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool, where said shaping tool further comprises at least one lumen defined therethrough and a vent communicated with said lumen.

28. An apparatus comprising:
a moldable sheath configured to at least temporarily retain a specific shape imparted to it; and
a shaping tool arranged and configured to be applied to said moldable sheath to impart said specific shape to said sheath while within a body cavity, which specific shape is held without continued assistance of said shaping tool, where said shaping tool further comprises a conductor disposed therethrough and an electrode coupled to said conductor for sensing or delivery of energy from said electrode.

29. An apparatus comprising:
a moldable sheath configured with sufficient moldability at body temperatures to at least temporarily retain a specific shape imparted to it; and
a lumen defined in said moldable sheath, where said sheath has at least one portion with a stiffness different than remaining portions of said sheath wherein the sheath is comprised of a relatively stiffer proximal portion and relatively stiffer distal portion extending to a distal tip with a relatively less stiff intermediate portion therebetween.

30. An apparatus comprising:
a moldable sheath with sufficient moldability at body temperatures to at least temporarily retain a specific shape imparted to it; and
a lumen defined in said moldable sheath, where said sheath has at least one portion with a moldability different than remaining portions of said sheath wherein the sheath is comprised of a relatively less moldable proximal portion and relatively less moldable distal portion extending to a distal tip with a relatively more moldable intermediate portion therebetween.

* * * * *